United States Patent
Kawakatsu

(10) Patent No.: US 6,922,065 B2
(45) Date of Patent: *Jul. 26, 2005

(54) COIL IMPENDANCE DETECTION METHOD AND OBJECT DETECTION METHOD AND APPARATUS USING THE SAME

(75) Inventor: Hiroshi Kawakatsu, Suita (JP)

(73) Assignee: Nohken Inc., Osaka (JP)

( * ) Notice: Subject to any disclaimer, the term of this patent is extended or adjusted under 35 U.S.C. 154(b) by 9 days.

This patent is subject to a terminal disclaimer.

(21) Appl. No.: 10/467,633

(22) PCT Filed: May 2, 2002

(86) PCT No.: PCT/JP02/04412
§ 371 (c)(1),
(2), (4) Date: Aug. 11, 2003

(87) PCT Pub. No.: WO02/090900
PCT Pub. Date: Nov. 14, 2002

(65) Prior Publication Data
US 2004/0061511 A1 Apr. 1, 2004

(30) Foreign Application Priority Data
May 8, 2001 (JP) .......................... 2001-136901

(51) Int. Cl.⁷ .......................... G01R 27/02; G01H 1/00
(52) U.S. Cl. ........................ 324/707; 73/579; 73/209 V
(58) Field of Search ................................ 324/707, 204, 324/207.11, 207.15, 207.22, 654, 655, 708, 713; 73/579, 290 R, 290 V, 643; 374/117–118

(56) References Cited

U.S. PATENT DOCUMENTS

| 3,270,274 | A | * | 8/1966 | Banks | 323/298 |
| 4,107,994 | A | * | 8/1978 | Sogo | 73/290 V |
| 4,309,902 | A | * | 1/1982 | Sano et al. | 73/159 |
| 4,740,726 | A | * | 4/1988 | Umezawa | 310/316.01 |
| 5,091,696 | A | * | 2/1992 | Roosen | 324/229 |
| 5,498,958 | A | * | 3/1996 | Tu et al. | 324/207.16 |
| 6,105,425 | A | * | 8/2000 | Kawakatsu | 73/290 V |
| 6,769,804 | B2 | * | 8/2004 | Kawakatsu | 374/118 |

FOREIGN PATENT DOCUMENTS

| JP | 05-87612 | 4/1993 |
| JP | 05-45887 | 7/1993 |
| JP | 09-236475 | 9/1997 |
| JP | 11-351944 | 12/1999 |

* cited by examiner

Primary Examiner—Anjan Deb
Assistant Examiner—Jeff Natalini
(74) Attorney, Agent, or Firm—McDermott Will & Emery LLP

(57) ABSTRACT

A triangular wave generating circuit (21) generates a sweep voltage of a triangular wave, a VCO (22) generates a sweep of a frequency according to the sweep voltage, and a driving coil (4) is driven by the sweep voltage. From the current flowing through the driving coil (4), an interference component is extracted and rectified by a rectifier circuit (27). A peak hold circuit (28) holds a peak value of an interference voltage within a period corresponding to one sweep. The peak value thus held is compared by a comparator circuit (29) with a predetermined value and accordingly, a relay circuit (30) outputs a signal indicative of whether an object is present or not.

12 Claims, 13 Drawing Sheets

COIL IMPENDANCE DETECTION METHOD AND OBJECT DETECTION METHOD AND APPARATUS USING THE SAME

PRIORITY DATA

This application is a National Stage Entry of PCT/JPO2/04412 filed on May 2, 2002, and claims foreign priority from application 2001-136901 filed in Japan on May 8, 2001.

TECHNICAL FIELD

The present invention relates to a method of detecting the impedance of an oscillation coil in a vibrating-type level sensor, and to a method and a device for detecting an object according to the coil impedance detecting method. More specifically, the present invention relates to a method of detecting the impedance of the oscillation coil by detecting a beat voltage caused by interference of an applied voltage generated when a frequency signal applied to the oscillation coil is swept at a rapid rate and a counter-electromotive force, and relates to a method and a device for detecting an object according to the coil impedance detecting method.

BACKGROUND ART

FIGS. 18A–18C show a schematic block diagram of a conventional vibrating-type level sensor disclosed in Japanese Patent Laying-Open No. 11-351944. Referring to FIG. 18A, a detection pipe unit 1 has its base 11 serving as a fixed end and its leading end closed with a closing unit 12 to serve as a free end, and accordingly constitutes a folded cantilever. A thin rectangular vibrating plate 2 is provided within detection pipe unit 1. Specifically, one end of vibrating plate 2 is fastened to closing unit 12 of detection pipe unit 1 and the other end thereof is provided with a permanent magnet 3 to serve as a free end.

In addition, an electromagnet 4 is attached closely to the inner wall of detection pipe unit 1 to face vibrating plate 2 in the direction of axis thereof. Electromagnet 4 is driven by an alternating current to generate a magnetic field. Between this magnetic field and a magnetic field of permanent magnet 3, an attracting/repelling action is produced to cause oscillations of the folded cantilever having vibrating plate 2, closing unit 12 and detecting pipe 1 with base 11 serving as the fixed end.

A distortion detecting element 5 is provided on the inner wall at base 11 of detection pipe unit 1. Distortion detecting element 5 detects the state of oscillation amplitude at base 11 of detection pipe 1 to convert the oscillation amplitude into an electric signal and supply the electric signal to an amplifier circuit 6. Amplifier circuit 6 amplifies the supplied signal and provides the amplified signal again to electromagnet 4.

Suppose that there is a relation as shown in FIG. 18B between the polarity of current applied to electromagnet 4 and a magnetic field generated at electromagnet 4. Then, the pole of electromagnet 4 that faces permanent magnet 3 is the north pole and thus attracting force is generated between this north pole and the south pole of permanent magnet 3 attached to vibrating plate 2 while repelling force is generated between the north pole of permanent magnet 3 and the north pole. Consequently, the free end of vibrating plate 2 is forced and displaced upward in FIG. 18B.

On the contrary, suppose that the current applied to electromagnet 4 has the opposite polarity. Then, as shown in FIG. 18C, the pole of electromagnet 4 that faces permanent magnet 3 is of the opposite polarity, i.e., the south pole. Accordingly, this south pole repels the south pole of the permanent magnet of vibrating plate 2 while the south pole and the north pole of the permanent magnet attract each other so that the free end of vibrating plate 2 is forced downward to cause change in the oscillation state. In this way, the polarity of current applied to electromagnet 4 may be changed according to the natural frequency of the vibrating system of the folded cantilever to produce and sustain oscillations.

According to the example shown in FIGS. 18A–18C, oscillations of the vibrating system are detected by detecting element 5 and then converted into an electric signal which is amplified by amplifier circuit 6 and supplied again to electromagnet 4, while a detecting circuit 7 outputs a detection signal. A piezoelectric element or acceleration pickup may be employed as oscillation detecting element 5. The piezoelectric element, however, has problems in that the piezoelectric element is brittle, the piezoelectric element attached to the detection pipe with an adhesive is susceptible to environment and temperature characteristics, and thus the reliability of the piezoelectric element itself is low.

Instead, a method may be used with a detecting circuit disclosed in Japanese Patent Laying-Open No. 5-87612 for example. According to this method, a phase comparator circuit, a loop filter (integrating circuit) and a voltage-controlled oscillator circuit (VCO circuit) constitute a PLL circuit. Pre-oscillator circuit generates an oscillation frequency according to an object to be detected, and the oscillation frequency is supplied to the phase comparator circuit of the PLL circuit. The oscillation frequency is then compared with a frequency signal of the VCO circuit to detect the object.

As for the above-described conventional examples, however, the detecting circuit has a relatively larger number of components, resulting in problems of greater cost, increased complexity of the structure and increase in the number of assembly steps. Such a large number of components also results in deterioration in reliability.

One chief object of the present invention is therefore to provide a method of detecting the impedance of an oscillation coil in a vibrating-type level sensor, according to which a beat voltage is detected that is caused by interference of an applied voltage and a counter-electromotive force, the applied voltage being generated when a frequency signal is swept at a rapid rate, and the magnitude of the beat voltage is used to determine whether there is a particulate matter or not, and to provide a method and a device for detecting an object according to the impedance detecting method.

DISCLOSURE OF THE INVENTION

The present invention is a method of detecting impedance of a driving coil of an electromagnet at an oscillation frequency of the driving coil provided to face a magnet with a tiny gap therebetween, the magnet being provided to a vibrating plate within a detection pipe. An alternating current of a frequency equal to a resonance frequency of the vibrating plate is applied to the driving coil to continuously monitor change in the impedance of the driving coil with respect to magnitude and phase of current flowing through the driving coil and thereby detect the degree of the change.

Another invention is a method of detecting impedance of a driving coil of an electromagnet at an oscillation frequency of the coil provided to face a magnet with a tiny gap therebetween, the magnet being provided to a vibrating plate within a detection pipe. An alternating current of a frequency with a sweep varying in a range including and close to a resonance frequency of the vibrating plate is applied to the driving coil to measure a change in the impedance of the driving coil being applied with the alternating current of the frequency with the sweep.

Still another invention is a method of detecting impedance of a driving coil of an electromagnet at an oscillation frequency of the driving coil provided to face a magnet with a tiny gap therebetween, the magnet being provided to a vibrating plate within a detection pipe. An alternating current of a frequency with a sweep varying in a range including and close to a resonance frequency of the vibrating plate is applied to the driving coil to output a detection signal according to a magnitude of an interference component generated by applying the alternating current of the frequency with the sweep.

A further invention is a method of detecting presence/absence of an object by detecting impedance of a driving coil of an electromagnet at an oscillation frequency of the driving coil provided to face a magnet with a tiny gap therebetween, the magnet being provided to a vibrating plate within a detection pipe. An alternating current of a frequency equal to a resonance frequency of the vibrating plate is applied to the driving coil to continuously monitor change in the impedance of driving coil with respect to magnitude and phase of current flowing through the driving coil and thereby detect the degree of the change, and the detected change in the impedance is compared with a reference value to detect presence/absence of the object.

A further invention is a method of detecting presence/absence of an object by detecting impedance of a driving coil of an electromagnet at an oscillation frequency of the driving coil provided to face a magnet with a tiny gap therebetween, the magnet being provided to a vibrating plate within a detection pipe. An alternating current of a frequency with a sweep varying in a range including and close to a resonance frequency of the vibrating plate is applied to the driving coil to measure a change in the impedance of the driving coil being applied with the alternating current of the frequency with the sweep, and a maximum value of the measured change in the impedance under the sweep is compared with a reference value to detect presence/absence of the object.

A further invention is a method of detecting presence/absence of an object by detecting impedance of a driving coil of an electromagnet at an oscillation frequency of the driving coil provided to face a magnet with a tiny gap therebetween, the magnet being provided to a vibrating plate within a detection pipe. An alternating current of a frequency with a sweep varying in a range including and close to a resonance frequency of the vibrating plate is applied to the driving coil to compare a magnitude of an interference component generated by applying the alternating current of the frequency with the sweep with a reference value and thereby detect presence/absence of the object.

A further invention is a device for detecting presence/absence of an object by detecting impedance of a driving coil of an electromagnet at an oscillation frequency of the driving coil provided to face a magnet with a tiny gap therebetween, the magnet being provided to a vibrating plate within a detection pipe. The device includes an alternating current application circuit applying an alternating current of a frequency equal to a resonance frequency of the vibrating plate to the driving coil, an impedance change detecting circuit continuously monitoring change in the impedance of the driving coil with respect to magnitude and phase of current flowing through the driving coil applied with the alternating current, and thereby detecting the degree of the change, and an object detecting circuit comparing the detected change in the impedance with a reference value to detect presence/absence of the object.

A further invention is a device for detecting presence/absence of an object by detecting impedance of a driving coil of an electromagnet at an oscillation frequency of the driving coil provided to face a magnet with a tiny gap therebetween, the magnet being provided to a vibrating plate within a detection pipe. The device includes an alternating current application circuit applying an alternating current of a frequency with a sweep varying in a range including and close to a resonance frequency of the vibrating plate to the driving coil, an impedance change measuring circuit measuring a change in the impedance of the driving coil being applied with the alternating current of the frequency with the sweep by the alternating current application circuit, and an object detecting circuit comparing a maximum value of the change in the impedance under the sweep that is measured by the impedance change measuring circuit with a reference value to detect presence/absence of the object.

A further invention is a device for detecting presence/absence of an object by detecting impedance of a driving coil of an electromagnet at an oscillation frequency of the driving coil provided to face a magnet with a tiny gap therebetween, the magnet being provided to a vibrating plate within a detection pipe. The device includes an alternating current application circuit applying an alternating current of a frequency with a sweep varying in a range including and close to a resonance frequency of the vibrating plate to the driving coil, an interference component extracting circuit extracting a magnitude of an interference component generated by applying the alternating current of the frequency with the sweep, and an object detecting circuit comparing the interference component extracted by the interference component extracting circuit with a reference value to detect presence/absence of the object.

BEST MODES FOR CARRYING OUT THE INVENTION

Figure 1:
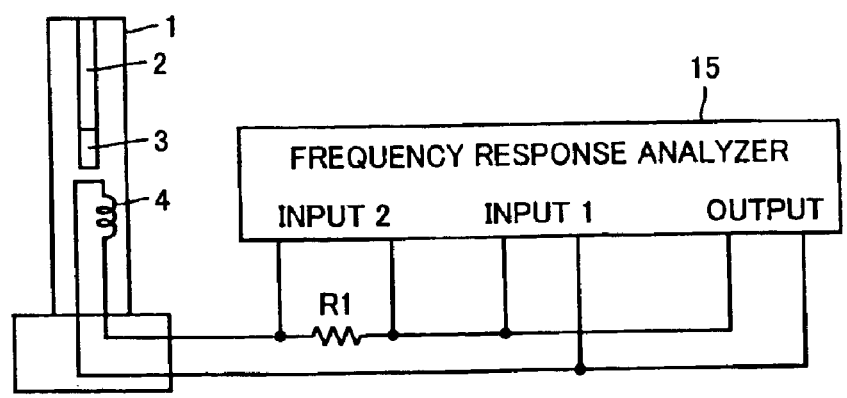
FIG. 1 illustrates principles of the present invention.
Figure 2A:
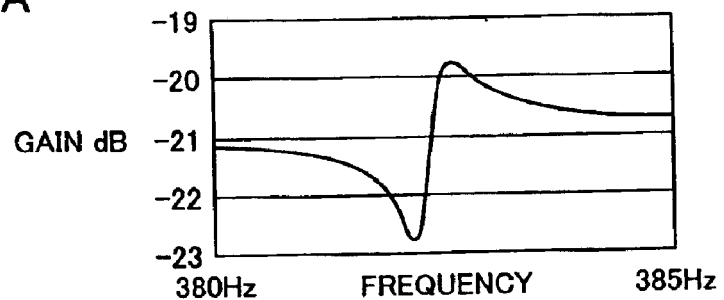
FIGS. 2A and 2B show a state of free oscillations with nothing detected.
Figure 2B:
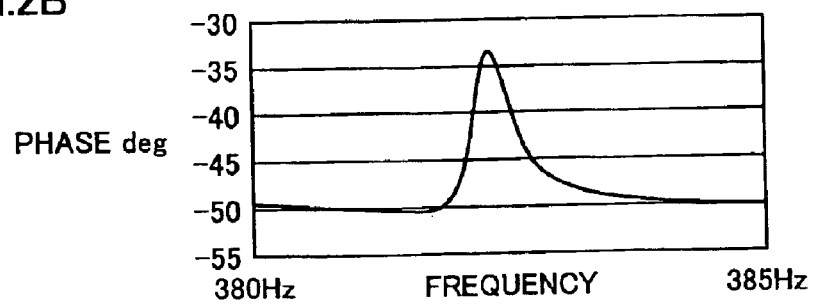
Figure 18A:
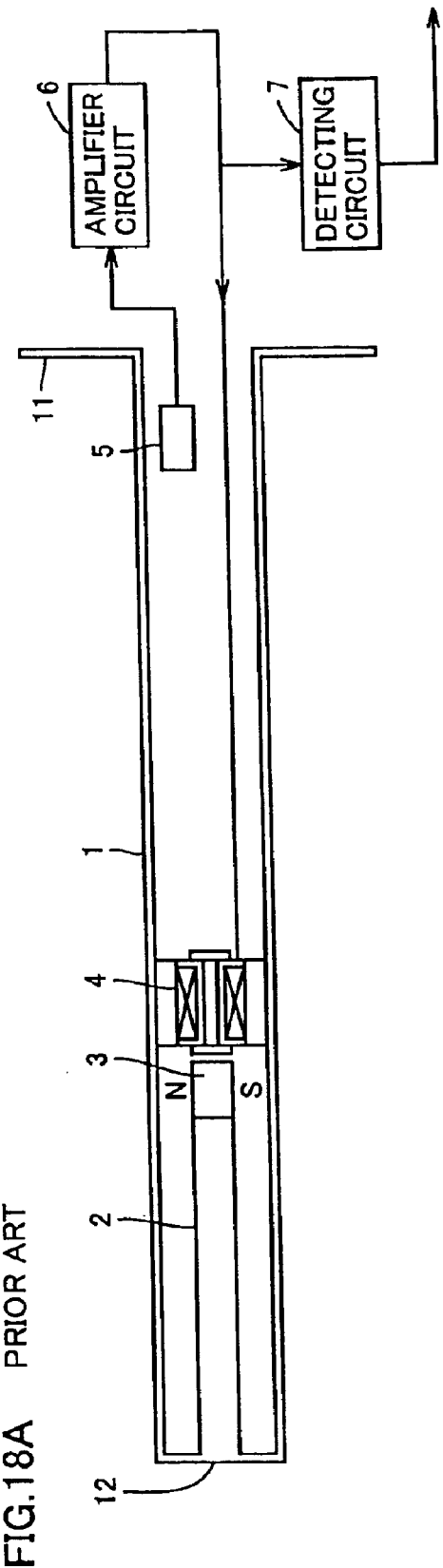
FIGS. 18A–18C show a schematic block diagram of a conventional vibrating-type level sensor.
Figure 18C:
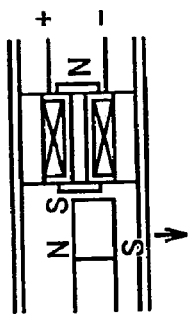
Figure 18B:
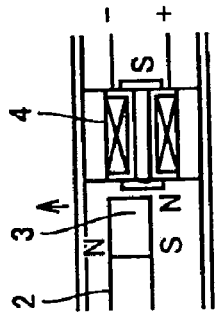

Description is now given with reference to FIG. 1 concerning principles of the present invention, prior to description of embodiments of the present invention. Referring to FIG. 1, a detection pipe 1, a vibrating plate 2, a permanent magnet 3 and a driving coil 4 are structured in the same manner as that of the conventional example shown in FIGS. 18A–18C. Here, a frequency of 380 Hz is selected as a resonance frequency of vibrating plate 2, and driving coil 4 is formed of 1440 turns of wire of 0.12 φ wound around an iron core to produce oscillations of vibrating plate 2.

Driving coil 4 has one end connected via a resistor R1 (10 Ω) to a first input terminal and an output terminal of a frequency resonance analyzer (FRA) 15, and resistor R1 has its two ends both connected to second input terminals of FRA 15. An output voltage of the output terminal of FRA 15 is set at 10Vp-p. The frequency of the FRA is swept from 300 Hz to 500 Hz to measure an input voltage of the first input terminal and measure the current flowing through resistor R1 and supplied to the second input terminals. FIGS. 2A–6B show resultant measurements.

Figure 3A:
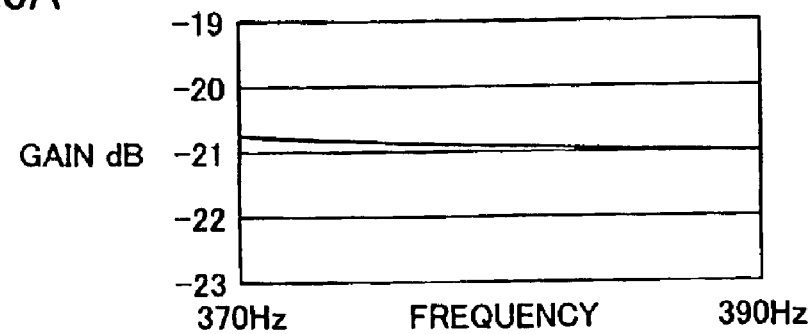
FIGS. 3A and 3B show a state in which a particulate matter is detected.
Figure 3B:
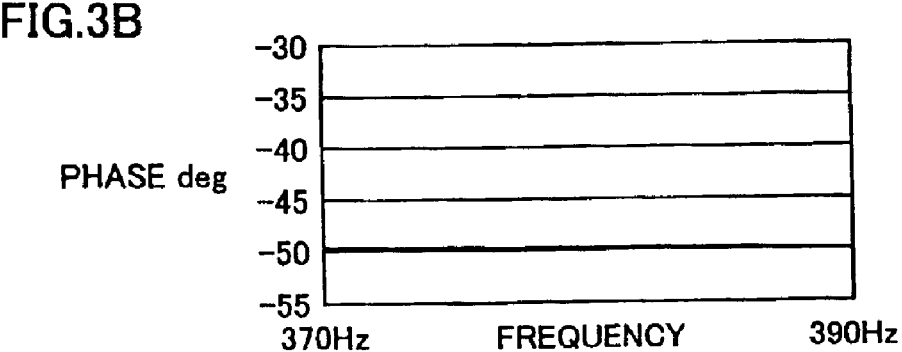
Figure 4A:
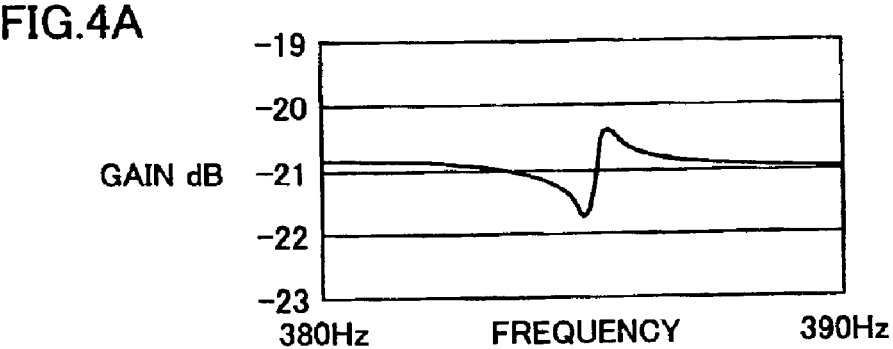
FIGS. 4A and 4B show a state in which water is detected.
Figure 4B:
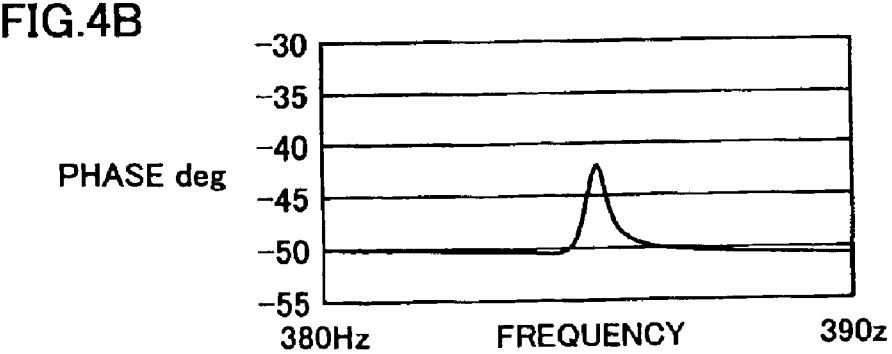
Figure 5A:
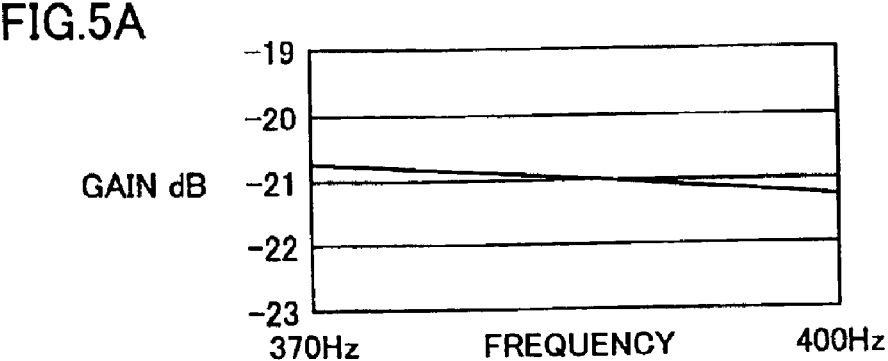
FIGS. 5A and 5B show a state in which the leading end of a detection pipe is fastened with a vise.
Figure 5B:
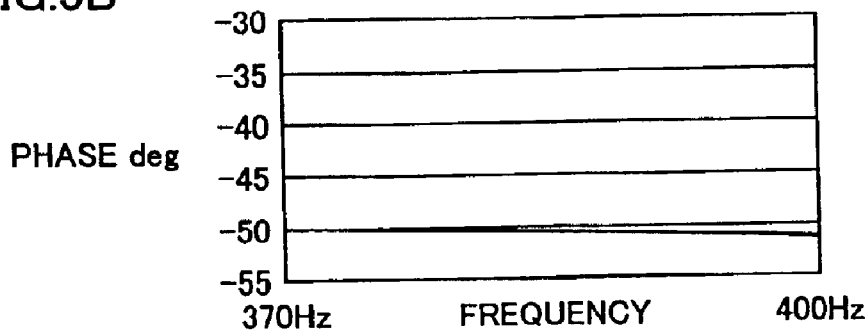
Figure 6A:
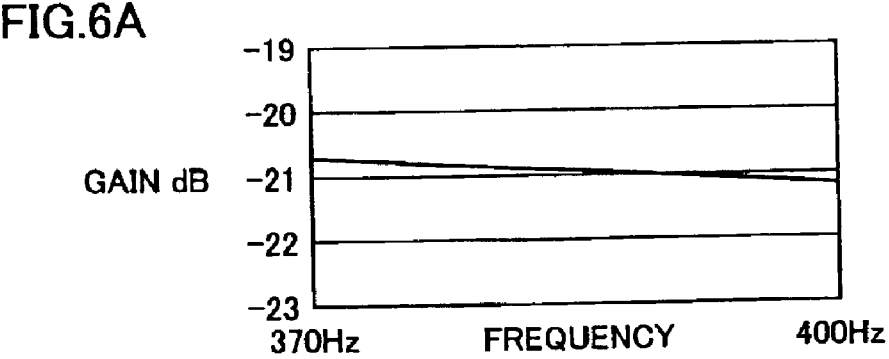
FIGS. 6A and 6B show a state in which the detection pipe is held in hand.
Figure 6B:
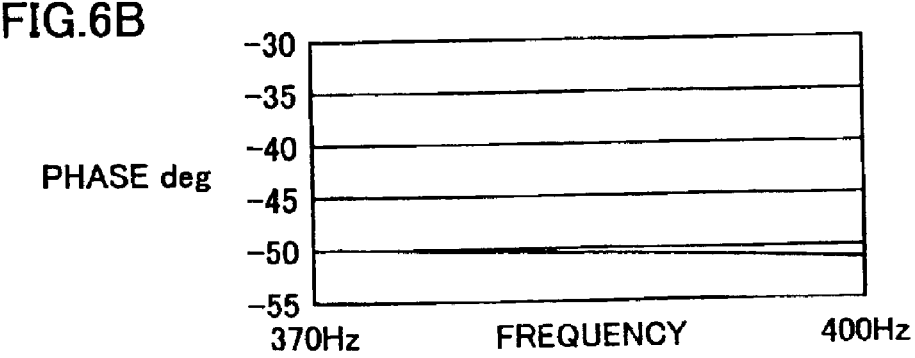

Of FIGS. 2A–6B, FIGS. 2A and 2B show a state of free oscillations with nothing detected, FIGS. 3A and 3B show a state in which a particulate matter is detected, FIGS. 4A and 4B show a state in which water is detected, FIGS. 5A and 5B show a state in which the leading end of detection pipe 1 is fastened with a vise, and FIGS. 6A and 6B show a state in which detection pipe 1 is held in hand.

Those drawings indicated by reference characters ending with letter A show the gain of the coil and those ending with letter B show the phase difference of the current flowing through the coil. For each state of this measurement, any frequency at which the gain and phase change to the greatest degree is set at the center based on which an appropriate frequency range is determined for taking measurements. For this reason, respective x-axes of the graphs represent different frequency ranges.

Referring to FIGS. 2A–6B, it is to be noted that change in the gain and phase occurs at the frequency of approximately 382 Hz and no change is found at other frequencies. From comparison of FIGS. 2A–6B, it is seen that the degree of change in gain and phase decreases as the physical constraint added to detection pipe 1 increases. On comparison between the state of free oscillations shown in FIGS. 2A and 2B and the state in which water is detected as shown in FIGS. 4A and 4B, it is found that the degree of change in gain and phase is smaller in the water-detecting state.

Moreover, no oscillation is produced in the state where the leading end of the detection pipe is fastened with the vise or held in hand as shown in FIGS. 5A–6B, and there is almost no change in gain and phase in the state where a particulate matter is detected as shown in FIGS. 3A and 3B. Accordingly, it has been ascertained that these states can clearly be distinguished from the state of free oscillations.

Figure 7:
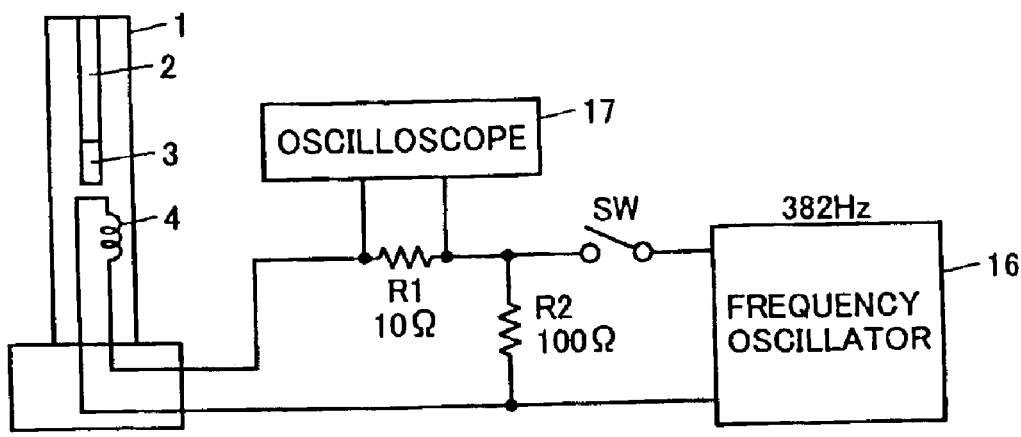
FIG. 7 illustrates a method of measuring a waveform observed when a burst wave is supplied to a driving coil shown in FIG. 1 and thereafter the supply is stopped.
Figure 8:
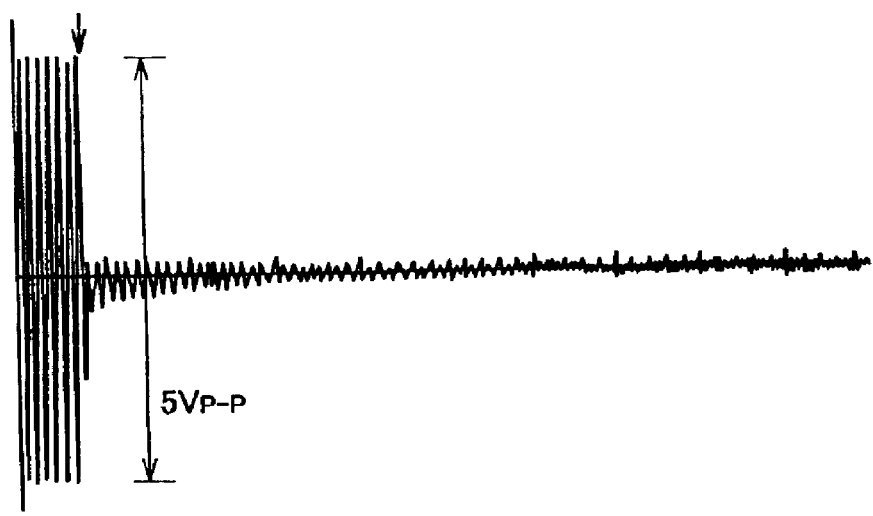
FIG. 8 is a waveform chat observed when the burst wave is supplied to the driving coil and thereafter the supply is stopped.
Figure 9:
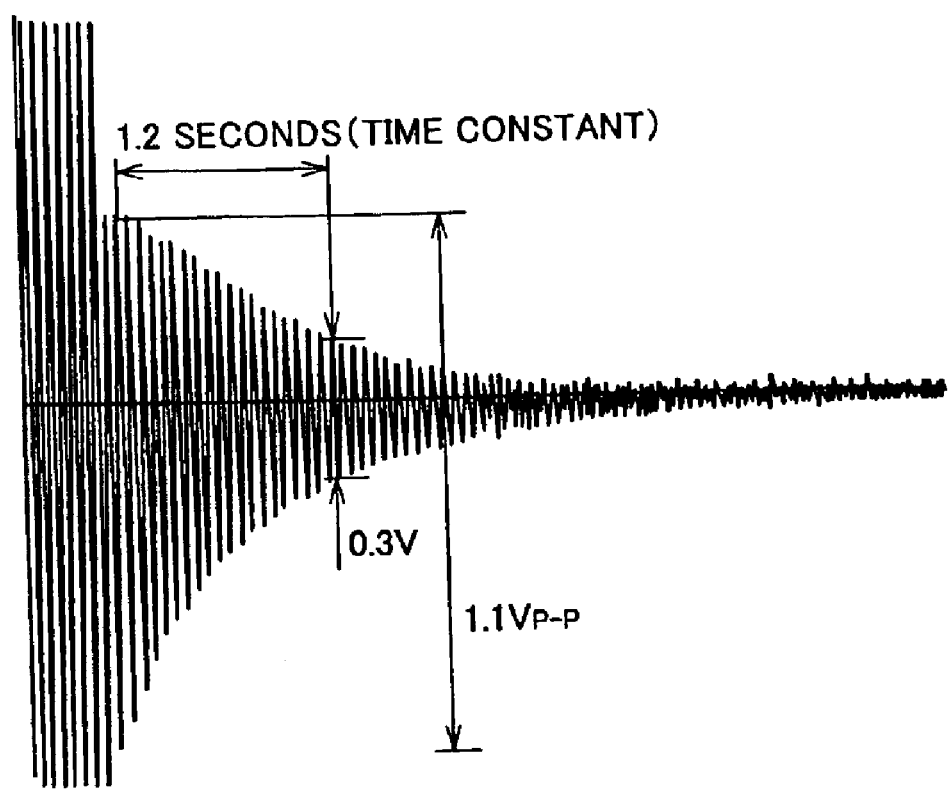
FIG. 9 shows the waveform shown in FIG. 8 in an enlarged form.

FIG. 7 illustrates a method of measuring a waveform observed when a burst wave is supplied to the driving coil shown in FIG. 1 and thereafter the supply is stopped, FIG. 8 is a waveform chart illustrating the waveform, and FIG. 9 is an enlarged version of the waveform shown in FIG. 8.

As shown in FIG. 7, a resistor R1 (10 Ω) and a resistor R2 (100 Ω) are connected in series to driving coil 4. A frequency oscillator generates a sine wave of 382 Hz to be supplied to driving coil 4 via a switch SW and resistor R1, and two ends of resistor R1 are both connected to an oscilloscope 17. Switch SW is turned on to supply the sine wave of 382 Hz to driving coil 4 with 5Vp-p so as to drive the electromagnet. Accordingly, repeated repelling/attracting action between an alternating magnetic field generated at the electromagnet and a magnetic field of permanent magnet 3 produces a vibrating force at the frequency of 382 Hz to be applied to vibrating plate 2. When the cycle of the vibrating force matches the mechanical oscillation frequency of vibrating plate 2, the oscillation amplitude of vibrating plate 2 reaches the maximum according to the left-hand rule. FIG. 8 shows a resultant resonance waveform with a peak of 5Vp-p indicated on oscilloscope.

When switch SW is turned off, no magnetic field is exerted from driving coil 4 on permanent magnet 3, so that the resonance of vibrating plate 2 is stopped. Then, although the resonance waveform should disappear from the waveform on oscilloscope 17 when switch SW is turned off, there is indicated a waveform with tiny waves.

This is for a reason as described below. Even if the supply of the sine wave to driving coil 4 is stopped, vibrating plate 2 and permanent magnet 3 stay mechanically in the state of free oscillations to continue oscillating because of the inertia of the preceding resonance. Oscillations of vibrating plate 2 allow permanent magnet 3 to continue oscillating, so that driving coil 4 acts to generate power which then produces an electromotive force. The electromotive force causes an electric current to flow through the path of resistors R1 and R2. As a result, the waveform through driving coil 4 that is measured by oscilloscope indicates, as shown in FIG. 8, that the voltage does not drop to 0 immediately after switch SW is turned off but decreases approximately to 1.1Vp-p and then gradually attenuates.

FIG. 9 shows the state of attenuation of the waveform in an enlarged form. As shown in FIG. 9, at the instant when switch SW is turned off, the voltage of 5Vp-p decreases to 1.1Vp-p and thereafter to 0.3Vp-p with a time constant of approximately 1.2 seconds. This attenuation of the waveform matches the state in which oscillations of vibrating plate 2 attenuate.

When the magnetic field of driving coil 4 causes the resonance of vibrating plate 2 at the resonance frequency, oscillations of permanent magnet 3 generate a counter-electromotive force at driving coil 4 in the direction of blocking the current flowing through driving coil 4. Because of this, it is considered that the impedance changes where resonance occurs. However, if there is no matching in frequency, vibrating plate 2 does not oscillate. Then, even if the same current flows through driving coil 4, the counter-electromotive force is not generated since vibrating plate 2 does not oscillate and current flows through driving coil 4 without being blocked. The impedance thus varies depending on whether vibrating plate 2 oscillates or not even for the same current. Whether any object is present or not is thus determined from difference between the current flowing through driving coil 4 in the state in which free oscillations of vibrating plate 2 occur and the current flowing therethrough in the state in which any object imposes constraint on oscillations thereof.

However, vibrating plate 2 has a significantly high Q, which is converted into a bandwidth for driving the driving coil 4 to cause resonance of vibrating plate 2 (the bandwidth being within a range from the peak to (peak minus 3 dB)). Then, the resonance frequency is within 1 Hz. In other words, if vibrating plate 2 oscillates at 300 Hz, no oscillation of vibrating plate 2 occurs at 298 Hz or 302 Hz. In theory, the oscillator may generate a frequency equal to the resonance frequency of vibrating plate 2 to drive driving coil 4 all the time and measure the current flowing through driving coil 4 in order to determine whether any object is present or not.

Actually, however, because of temperature characteristics of vibrating plate 2 at the resonance frequency, temperature characteristics of the oscillator and mechanical variations of detection pipe 1, variation of the resonance frequency to a certain degree is unavoidable. For this reason, it is considerably difficult to determine presence/absence of an object is present or not with a fixed frequency.

Then, the frequency is swept that is within a certain range having the frequency of vibrating plate 2 at the center. If there is a change in current, presence/absence of an object may be detected.

Figure 10:
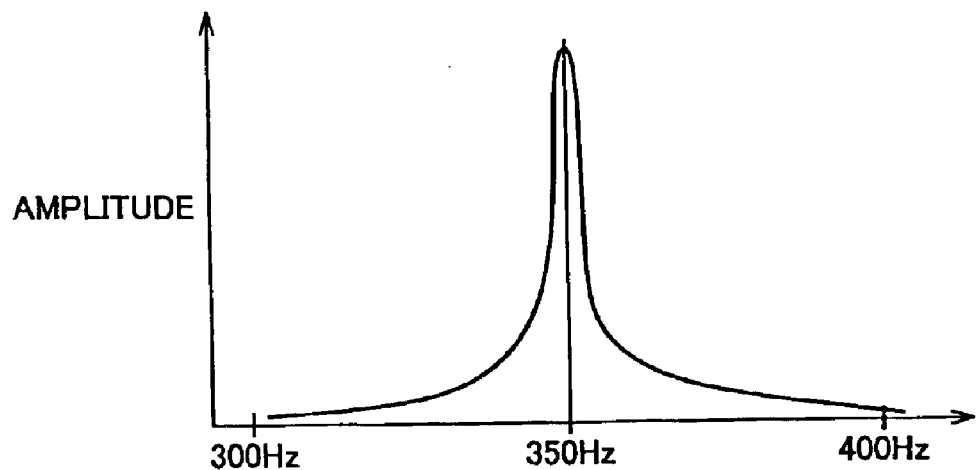
FIG. 10 shows a relation between the amplitude and frequency when a sweep signal of 300-400 Hz is supplied to a vibrating plate.

FIG. 10 shows a relation between the amplitude and frequency when a sweep signal from 300 Hz to 400 Hz is supplied to vibrating plate. As shown in FIG. 10, the resonance frequency of vibrating plate is set for example at 350 Hz. The frequency of the signal supplied to vibrating plate is increased gradually from 300 Hz. Then, resonance of vibrating plate 2 is started at approximately 350 Hz. The resonance attains the peak and thereafter attenuates gradually. The frequency range where the resonance occurs is within 1 Hz as described above. A greater frequency range would be advantageous for measurement, however, it takes time to start oscillations since vibrating plate 2 itself is a mechanical system. The time required for starting oscillations of detection pipe 1 and vibrating plate 2 is thus a few seconds (the time from application of the resonance frequency of vibrating plate to the electromagnet, to occurrence of oscillations to a sufficient degree). For example, if it takes a second to sweep 1 Hz, the time required for sweeping from 300 Hz to 400 Hz is 100 seconds. Such a device is not actually appropriate for detecting presence/absence of an object. A method for sweeping the frequency at a rapid rate for the vibrating plate is now considered.

Figure 11:
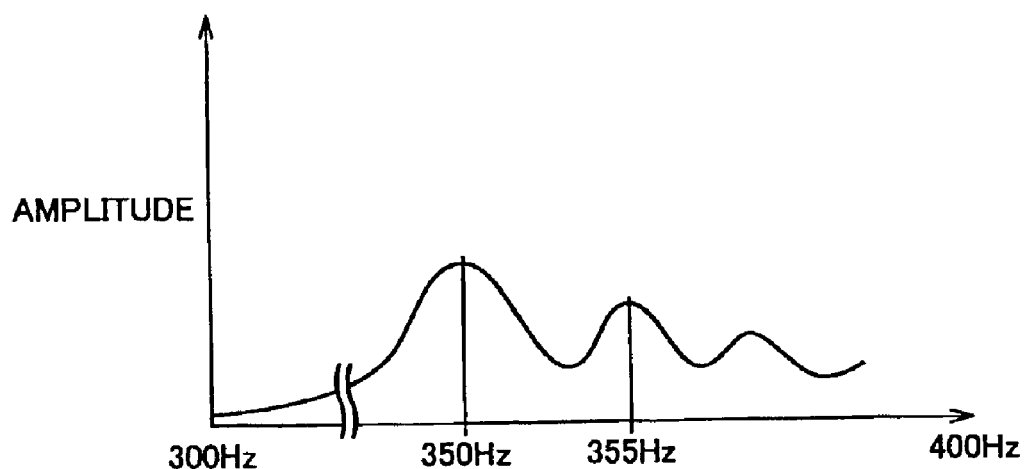
FIG. 11 shows a relation between the amplitude and frequency when a frequency is swept at a rapid rate and supplied to the vibrating plate.

FIG. 11 shows a relation between the amplitude and frequency when a frequency is swept at a rapid rate and applied to driving coil 4. The resonance frequency of vibrating plate 2 is set at 350 Hz, and a sweep signal in a range from 300 Hz to 400 Hz is provided for example in three seconds. Consequently, as shown in FIG. 11, vibrating plate 2 starts resonance when the sweep signal is 350 Hz since the natural resonance frequency of vibrating plate 2 is 350 Hz. However, shortly after this, the rapid rate of the sweep signal causes mismatch in frequency.

Even if the frequency of the sweep signal does not match to a slight degree, vibrating plate 2 continues oscillating at the resonance frequency for a certain time because of reverberation characteristics of the mechanical system. When the frequency of the sweep signal is for example 355 Hz, interference (beat) occurs between the natural oscillation frequency 350 Hz of vibrating plate 2 and the frequency 355 Hz of the sweep signal. Because of this, undulations of 8 Hz to 10 Hz are generated as shown in FIG. 11. It has been ascertained by experiment that the undulations occur without exception when a frequency is swept at a rate of 3 to 5 seconds for example and applied to driving coil 4. It is thus intended by the present invention that presence/absence of the undulations is detected for detecting presence/absence of an object.

Figure 12:
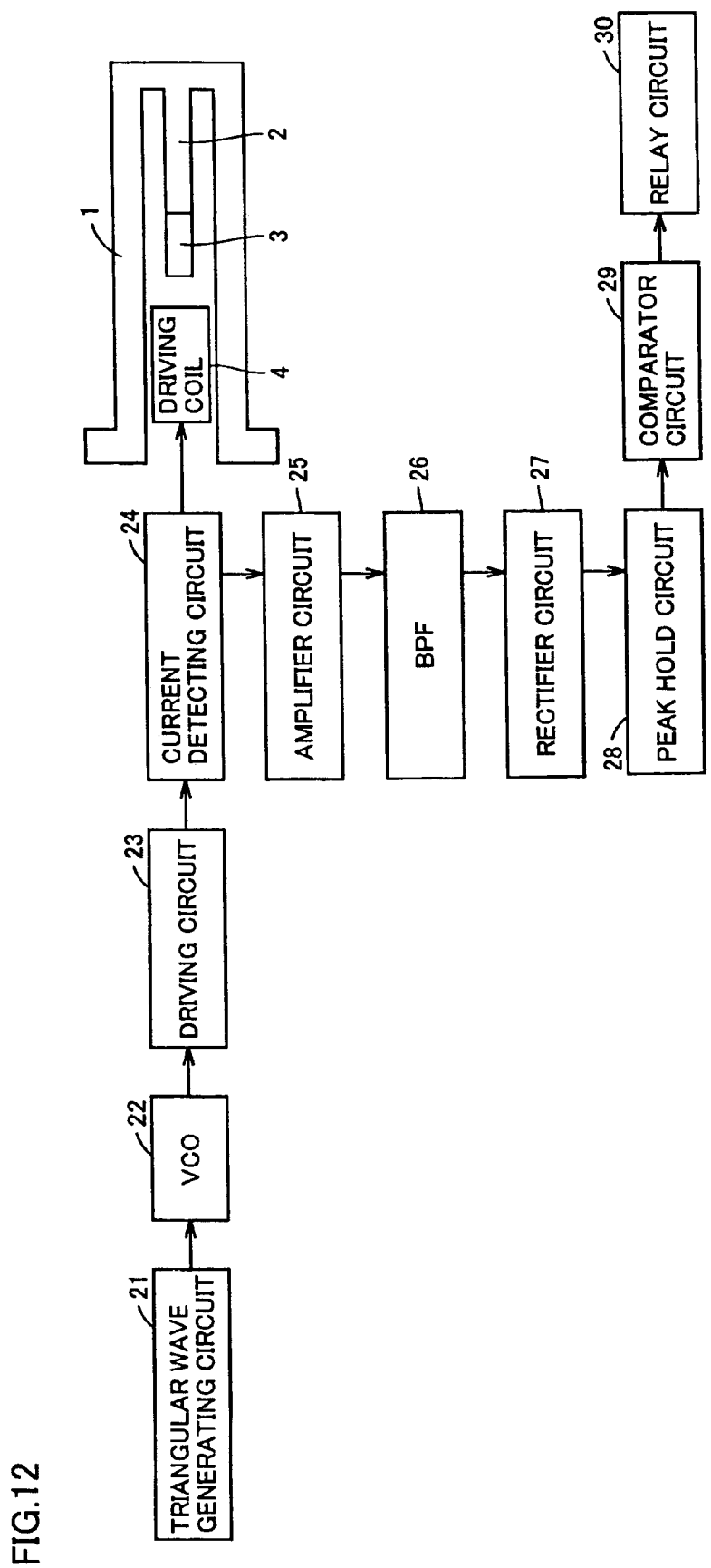
FIG. 12 is a block diagram of a first embodiment in accordance with the above-mentioned principles.

FIG. 12 is a specific block diagram according to the above-discussed principles. Referring to FIG. 12, a triangular wave generating circuit 21 generates a sweep voltage of a triangular wave and supplies the sweep voltage to a voltage-controlled oscillator (hereinafter referred to as VCO) 22. VCO 22 sweeps a frequency according to the sweep voltage to generate a sweep signal which is applied to driving coil 4. For example, VCO 22 may decrease the frequency if the amplitude of the triangular wave is small and increase the frequency if the amplitude is large. As discussed in connection with FIGS. 18A–18C, driving coil 4 constitutes the electromagnet, and other components, namely detection pipe 1, vibrating plate 2 and permanent magnet 3 are structured in the same manner as that shown in FIGS. 18A–18C.

According to this embodiment, VCO 22 sweeps a frequency from 300 Hz to 400 Hz for example. The signal swept by VCO 22 is amplified by a driving circuit 23 into a drive signal to drive driving coil 4 constituting the electromagnet within detection pipe 1, and the drive signal is supplied via a current detecting circuit 24 to driving coil 4. Current detecting circuit 24 detects the current flowing through the driving coil.

The current detected by current detecting circuit 24 is supplied to and amplified by an amplifier circuit 25, and only the frequency component of the interference component, i.e., interference voltage, as shown in FIG. 11 is extracted by a bandpass filter (hereinafter referred to as BPF) 26. The interference component is supplier to and rectified by a rectifier circuit 27 to extract only the positive (or negative) component of the interference voltage. A peak hold circuit 28 holds a peak value of the interference voltage within the time of one sweep. The peak value thus held is compared by a comparator circuit 29 with a predetermined value. If the peak value is larger than the predetermined value, it is determined that there is no object and resonance of vibrating plate 2 occurs, and accordingly a signal indicative of absence of an object is supplied from a relay circuit 30. On the contrary, if the peak value is smaller than the predetermined value, a signal indicative of presence of an object is supplied from relay circuit 30.

According to the discussion above, the held peak value is compared with the predetermined value to determine if an object is present or not. Alternatively, the state of an object may be determined. For example, the state of oscillations of vibrating plate 2 varies depending on the state of a medium to be detected. Namely, suppose that the medium is water. Then, the medium may be in the state of frozen water, in the state of water, or in the state of transition from water to frozen water. The predetermined value may be determined according to the state to be compared by comparator circuit 29. Alternatively, different degrees of the viscosity of the medium may be detected.

Figure 13:
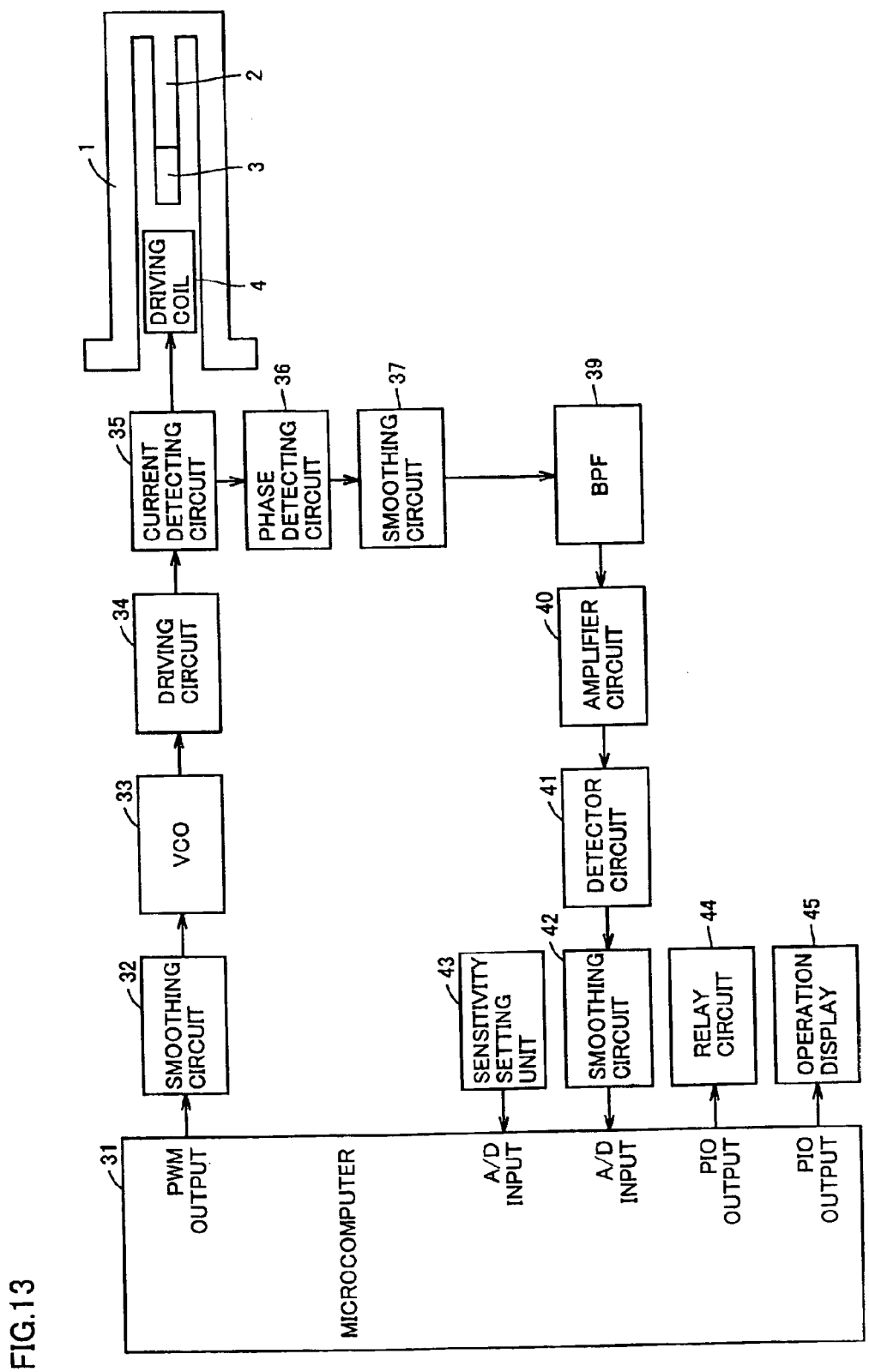
FIG. 13 is a block diagram according to a second embodiment of the present invention.

FIG. 13 is a block diagram according to another embodiment of the present invention. Referring to FIG. 13, a microcomputer 31 has a PWM (pulse width modulation) output which is supplied to and converted into a triangular-wave signal by a smoothing circuit 32. The triangular-wave signal is then provided to a VCO 33 and a sweep signal with a repeatedly changing frequency from 300 to 400 Hz is provided to a driving circuit 34 and the driving signal is supplied via a current detecting circuit 35 to a driving coil 4.

Current detecting circuit 35 detects the current flowing through driving coil 4 and the detection signal is provided to a phase detecting circuit 36. Phase detecting circuit 36 detects a change in fluctuation of the phase of the current flowing through driving coil 4. A signal indicative of this detection is supplied to and smoothed by a smoothing circuit 37 and a fluctuation component is output as a voltage change component.

Moreover, an interference component is extracted through a BPF 39 that is supplied to and amplified by an amplifier circuit 40. The amplified output is supplied to a detector circuit 41 where the interference component is extracted that is smoothed by a smoothing circuit 42 and supplied to an A/D input of microcomputer 31. Microcomputer 31 converts the interference component supplied to the A/D input into a digital signal and thereafter the peak value thereof is determined through software processing. Then, the peak value is compared with a predetermined value to output a signal indicative of presence/absence of an object to a relay circuit 44.

It is noted that a sensitivity setting unit 43, relay circuit 44 and an operation display 45 are connected to microcomputer 31. Sensitivity setting unit 43 sets a sensitivity for detecting the interference component.

Figure 14:
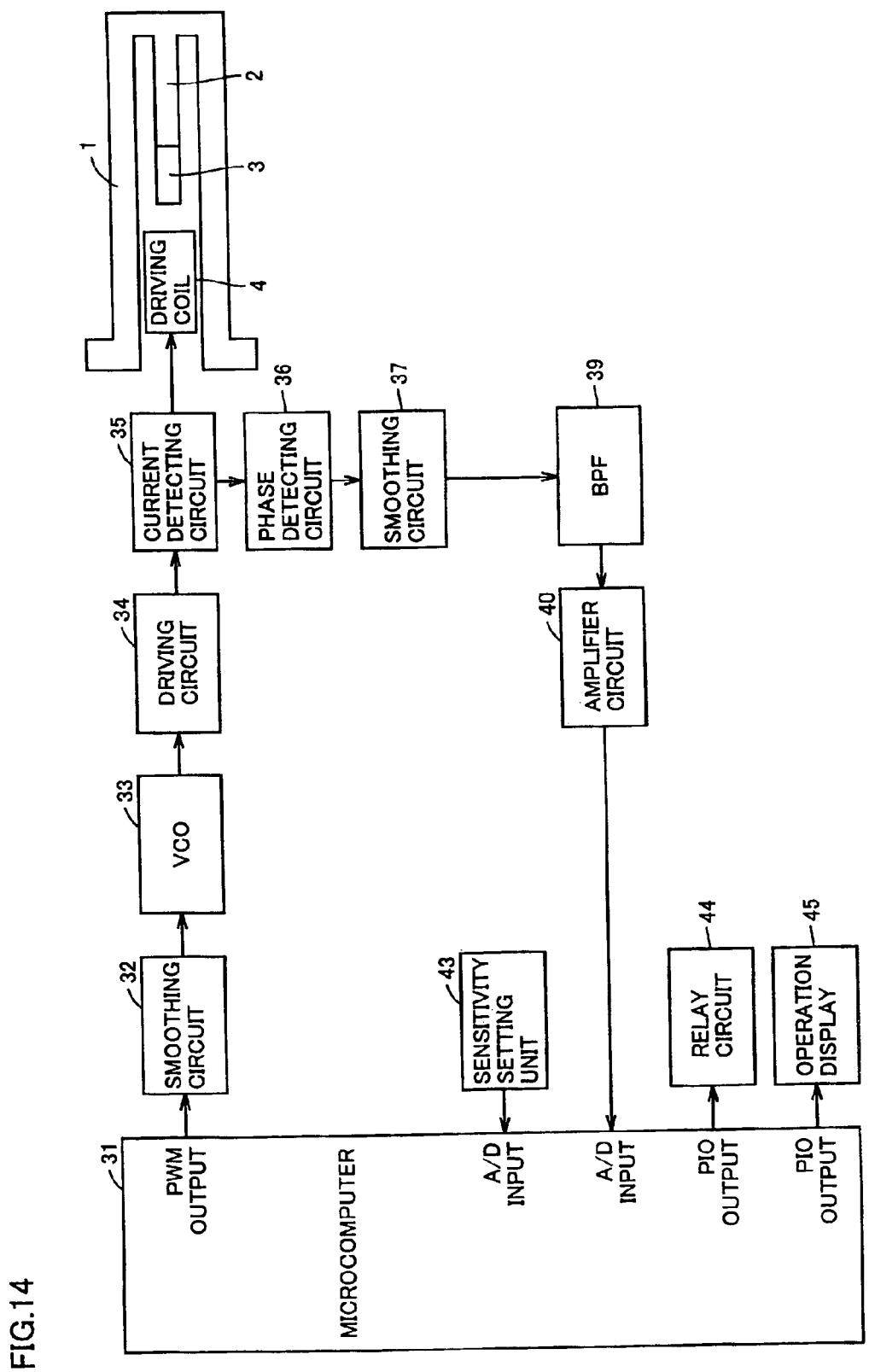
FIG. 14 is a block diagram according to a third embodiment of the present invention.

FIG. 14 is a block diagram according to a third embodiment of the present invention. The embodiment shown in FIG. 14 does not include detector circuit 41 and smoothing circuit 42 shown in FIG. 13. Here, an AC level signal output from an amplifier circuit 40 is directly supplied to an A/D input of a microcomputer 31 to perform a reading operation. The hardware structure may thus be simplified while it is required that A/D conversion should frequently be performed which then requires corresponding software.

Figure 15:
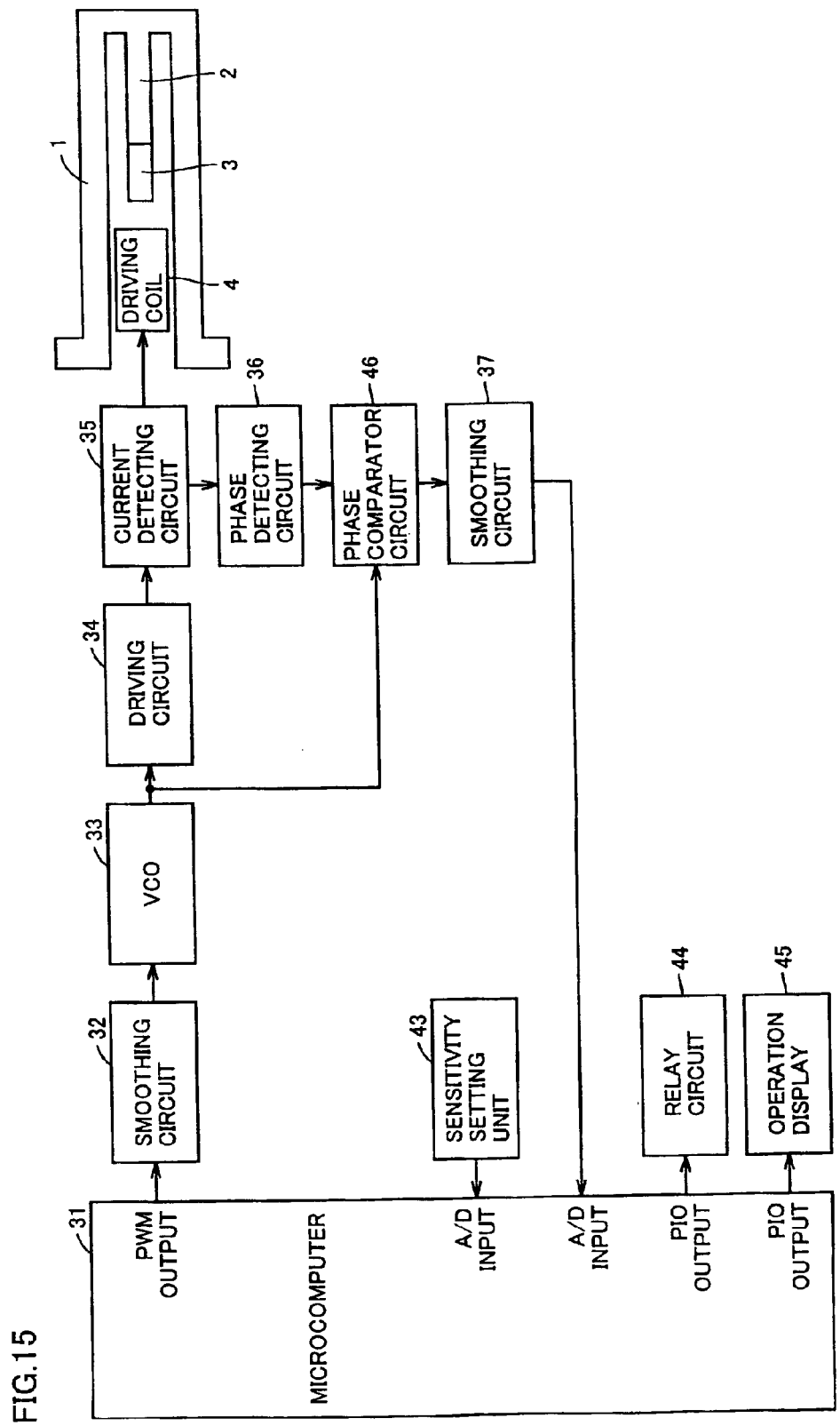
FIG. 15 is a block diagram according to a fourth embodiment of the present invention.

FIG. 15 is a block diagram according to a fourth embodiment of the present invention. According to this embodiment, a voltage applied to a driving circuit 34 and a change in the phase of a driving current detected by a phase detecting circuit 36 are directly provided to and compared with each other by a comparator circuit 46. An output indicative of this comparison is smoothed by a smoothing circuit 37 and then supplied to an A/D input of a microcomputer 31.

According to the embodiments shown in FIGS. 12–14, the phase produced by fluctuation due to interference is detected by phase detecting circuit 36. Here, in order to cause the fluctuation, a sweep of the frequency should dynamically be generated. On the other hand, according to the embodiment shown in FIG. 15, respective a phase of the waveform of the driving signal supplied to driving coil 4 is compared with a phase of the waveform of the detected current. This is advantageous in that the presence of a peak may statically be detected.

Figure 16:
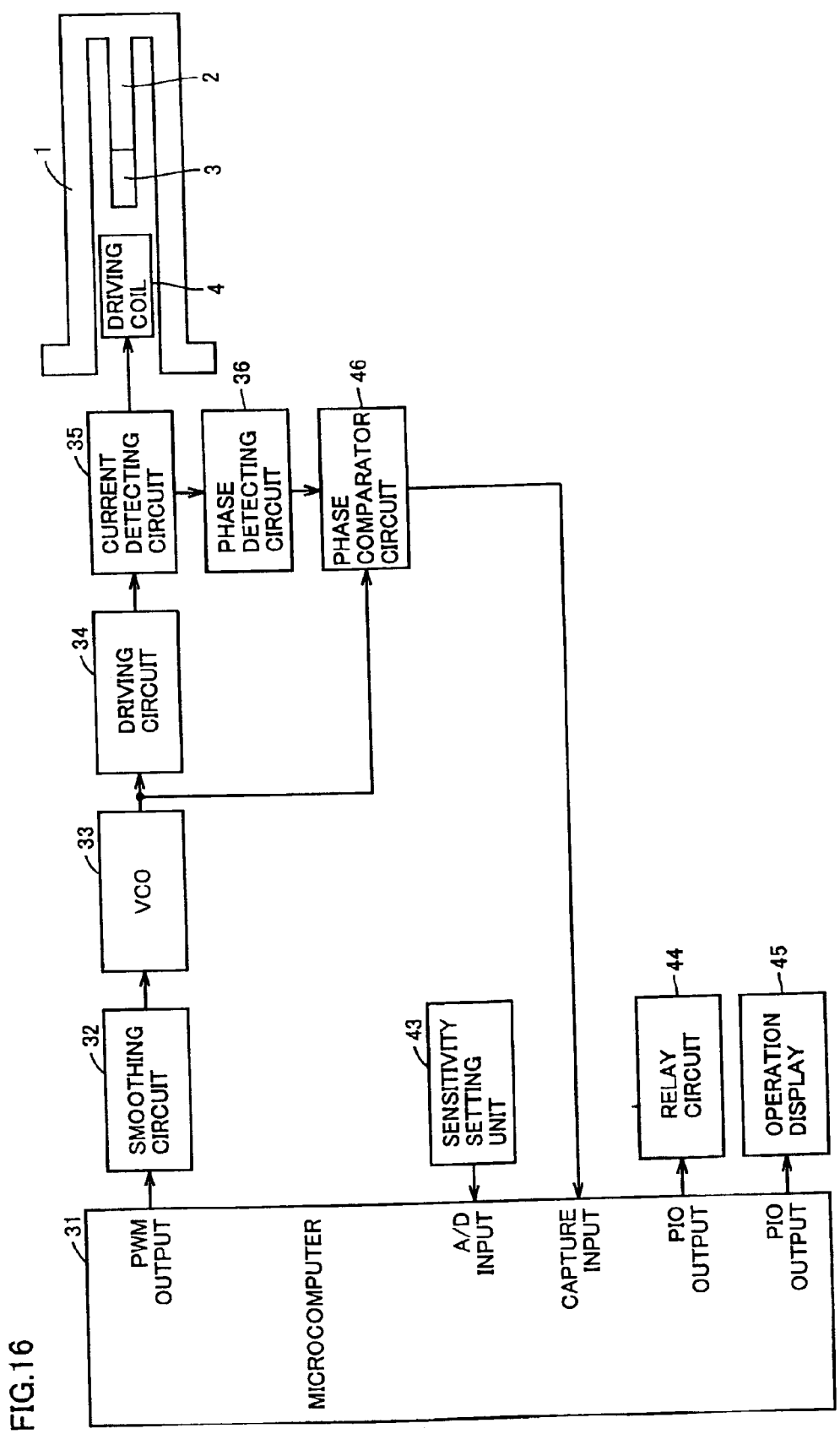
FIG. 16 is a block diagram according to a fifth embodiment of the present invention.

FIG. 16 is a block diagram according to a fifth embodiment of the present invention. According to this embodiment, there is included no smoothing circuit 37 shown in FIG. 15. Instead, an output from a phase comparator circuit 46 is directly provided to a capture input of a microcomputer 31 for detection. This embodiment has a characteristic that the point of resonance is correctly specified.

Figure 17:
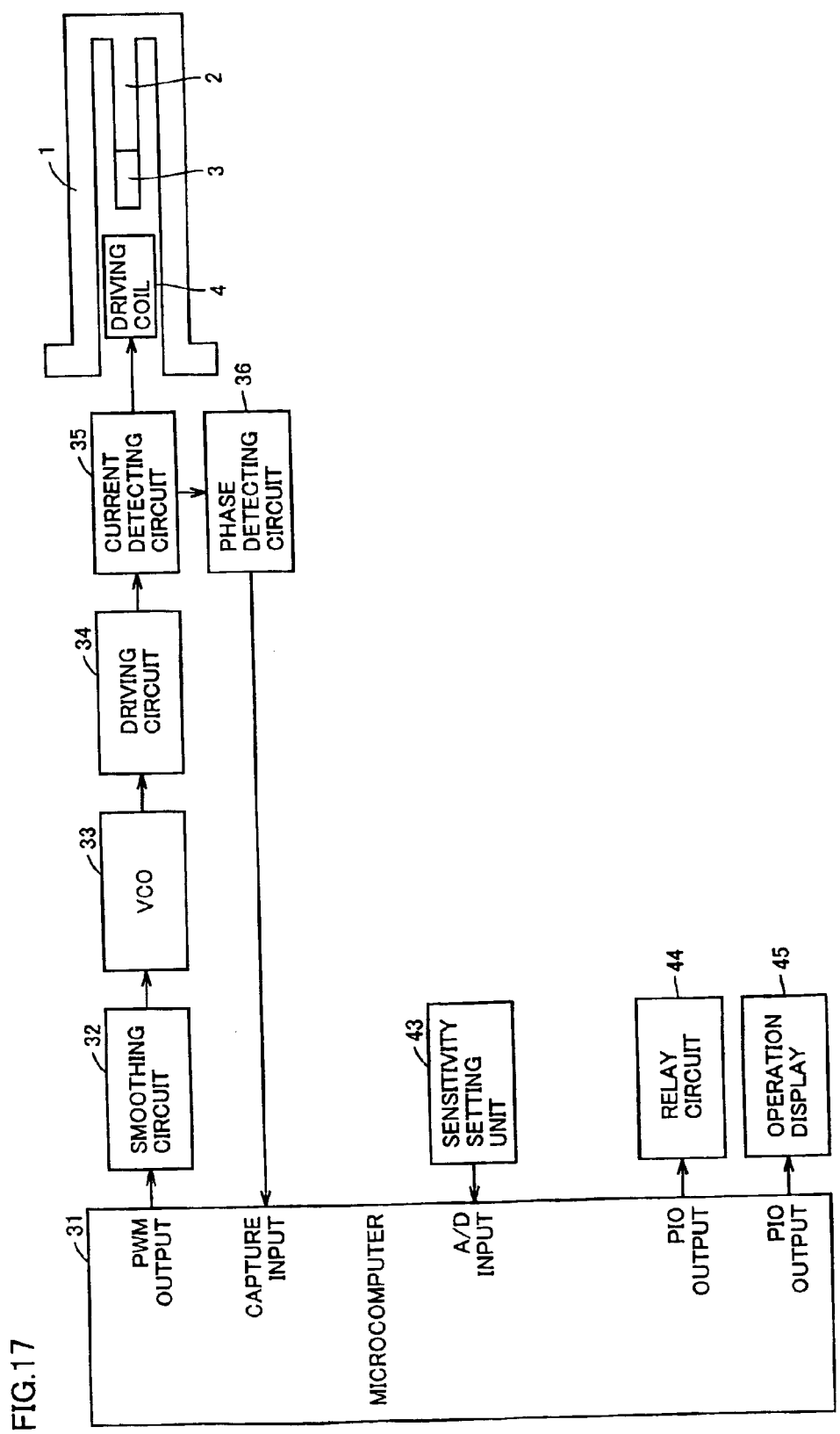
FIG. 17 is a block diagram according to a sixth embodiment of the present invention.

FIG. 17 is a block diagram according to a sixth embodiment of the present invention. According to this embodiment, a change in interference of the phase of the driving current that is detected by a phase detecting circuit 36 is directly supplied to a capture input of a microcomputer 31 for detection. This embodiment achieves the most simplified circuit configuration relative to the above-discussed embodiments while requiring a greater number of software processes.

Instead of the PWM output from microcomputer 31 shown in FIG. 17, a pulse output of an oscillation frequency or any frequency close to the oscillation frequency may be derived through program processing and, without smoothing circuit 32 and VCO 33, the pulse output may directly be supplied to driving circuit 34.

It should be understood that the embodiments disclosed herein are by way of illustration and example in every respect and are not to be taken by way of limitation. The scope of the present invention is defined not by the description above but by the scope of claims, and it is intended that all of the modifications within the meaning and range equivalent to the scope of claims are included.

As heretofore discussed, according to the present invention, the vibrating-type level sensor sweeps a frequency of the voltage to be applied to the electromagnet, the sweep having its center set at the resonance frequency of the vibrating plate. Because of a difference between the sweep frequency and mechanical oscillations of the vibrating body, interference occurs, and the interference causes a change in impedance of the coil in the electromagnet. The impedance change is detected and, based on the detected change in impedance, presence/absence of an object can be detected.

In this way, it can be determined whether an object is present or not by providing a sensor unit constituted of only the driving coil (electromagnet) and the permanent magnet while the conventional piezoelectric element or acceleration pickup is not employed for a receiving section of the sensor unit. The structure is thus simplified and the cost is remarkably cut, and the reliability of the device is accordingly enhanced.

INDUSTRIAL APPLICABILITY

The present invention is a method of detecting the impedance of an oscillation coil in a vibrating-type level sensor as well as a method and a device for detecting an object according to the coil impedance detecting method. The present invention is applied for example to a device for detecting a particulate matter within a tank by detecting a beat voltage caused by interference of an applied voltage and a counter-electromotive force, being generated when a frequency of the applied voltage to an oscillation coil is swept at a rapid rate, so as to detect the impedance of the oscillation coil.

What is claimed is:

1. A method of detecting impedance of a driving coil (4) at an oscillation frequency of said driving coil provided to face a magnet (3) with a tiny gap therebetween, said magnet being provided to a vibrating plate (2) within a detection pipe (1), wherein
   an alternating current of a frequency equal to a resonance frequency of said vibrating plate (2) is applied to said driving coil (4) to continuously monitor change in the impedance of said driving coil with respect to magnitude and phase of current flowing through said driving coil and thereby detect the degree of the change.

2. A method of detecting impedance of a driving coil (4) at an oscillation frequency of said driving coil provided to face a magnet (3) with a tiny gap therebetween, said magnet being provided to a vibrating plate (2) within a detection pipe (1), wherein an alternating current of a frequency being swept in a range including and close to a resonance frequency of said vibrating plate (2) is applied to said driving coil (4) to measure a change in the impedance of said driving coil (4) being applied with said alternating current of the frequency with the sweep.

3. A method of detecting impedance of a driving coil (4) at an oscillation frequency of said driving coil provided to face a magnet (3) with a tiny gap therebetween, said magnet being provided to a vibrating plate (2) within a detection pipe (1), wherein an alternating current of a frequency being swept in a range including and close to a resonance frequency of said vibrating plate (2) is applied to said driving coil (4) to output a detection signal according to a magnitude of an interference component generated by applying said alternating current of the frequency with the sweep.

4. A method of detecting presence/absence of an object by detecting impedance of a driving coil (4) at an oscillation frequency of said driving coil provided to face a magnet (3) with a tiny gap therebetween, said magnet being provided to a vibrating plate (2) within a detection pipe (1), wherein an alternating current of a frequency equal to a resonance frequency of said vibrating plate (2) is applied to said driving coil (4) to continuously monitor change in the impedance of said driving coil (4) with respect to magnitude and phase of current flowing through said driving coil and thereby detect the degree of the change, and said detected change in the impedance is compared with a reference value to detect presence/absence of the object.

5. A method of detecting presence/absence of an object by detecting impedance of a driving coil (4) at an oscillation frequency of said driving coil provided to face a magnet (3) with a tiny gap therebetween, said magnet being provided to a vibrating plate (2) within a detection pipe (1), wherein an alternating current of a frequency being swept in a range including and close to a resonance frequency of said vibrating plate (2) is applied to said driving coil (4) to measure a change in the impedance of said driving coil (4) being applied with said alternating current of the frequency with the sweep, and a maximum value of said measured change in the impedance under the sweep is compared with a reference value to detect presence/absence of the object.

6. A method of detecting presence/absence of an object by detecting impedance of a driving coil (4) at an oscillation frequency of said driving coil provided to face a magnet (3) with a tiny gap therebetween, said magnet being provided to a vibrating plate (2) within a detection pipe (1), wherein an alternating current of a frequency being swept in a range including and close to a resonance frequency of said vibrating plate (2) is applied to said driving coil (4) to compare a magnitude of an interference component generated by applying said alternating current of the frequency with the sweep with a reference value and thereby detect presence/absence of the object.

7. An object detecting device for detecting presence/absence of an object by detecting impedance of a driving coil (4) at an oscillation frequency of said driving coil provided to face a magnet (3) with a tiny gap therebetween, said magnet being provided to a vibrating plate (2) within a detection pipe (1), comprising:

an alternating current application circuit (21–23) applying an alternating current of a frequency equal to a resonance frequency of said vibrating plate (2) to said driving coil;

an impedance change detecting circuit (24–27) continuously monitoring change in the impedance of said driving coil with respect to magnitude and phase of current flowing through said driving coil applied with the alternating current by said alternating current application circuit, and thereby detecting the degree of the change; and an object detecting circuit (29) comparing the change in the impedance detected by said impedance change detecting circuit with a reference value to detect presence/absence of the object.

8. An object detecting device for detecting presence/absence of an object by detecting impedance of a driving coil (4) at an oscillation frequency of said driving coil provided to face a magnet (3) with a tiny gap therebetween, said magnet being provided to a vibrating plate (2) within a detection pipe (1), comprising:

an alternating current application circuit (21–23) applying an alternating current of a frequency being swept in a range including and close to a resonance frequency of said vibrating plate (2) to said driving coil (4);

an impedance change measuring circuit (24–27) measuring a change in the impedance of said driving coil being applied with said alternating current of the frequency with the sweep by said alternating current application circuit; and an object detecting circuit (29) comparing a maximum value of said change in the impedance under the sweep that is measured by said impedance change measuring circuit with a reference value to detect presence/absence of the object.

9. An object detecting device for detecting presence/absence of an object by detecting impedance of a driving coil (4) at an oscillation frequency of said driving coil provided to face a magnet (3) with a tiny gap therebetween, said magnet being provided to a vibrating plate (2) within a detection pipe (1), comprising:

an alternating current application circuit (21–23) applying an alternating current of a frequency being swept in a range including and close to a resonance frequency of said vibrating plate to said driving coil;

an interference component extracting circuit (26) extracting a magnitude of an interference component generated by applying said alternating current of the frequency with the sweep by said alternating current application circuit; and an object detecting circuit (29) comparing said interference component extracted by said interference component extracting circuit with a reference value to detect presence/absence of the object.

10. The object detecting device according to claim 9, wherein said interference component extracting circuit detects a phase difference of the interference caused by the frequency with the sweep and mechanical oscillations of a vibrating body.

11. The object detecting device according to claim 9, wherein said interference component extracting circuit detects a peak value of a phase of the interference caused by the frequency with the sweep and mechanical oscillations of a vibrating body.

12. The object detecting device according to claim 9, wherein said interference component extracting circuit detects current flowing through said driving coil to detect a phase difference or a peak value of a phase of the interference.

* * * * *